(12) United States Patent
Rafert

(10) Patent No.: US 6,497,659 B1
(45) Date of Patent: Dec. 24, 2002

(54) SYSTEM FOR IDENTIFYING A CABLE TRANSMITTING A SIGNAL FROM A SENSOR TO AN ELECTRONIC INSTRUMENT

(75) Inventor: Stephen C. Rafert, Kent, WA (US)

(73) Assignee: Spacelabs Medical, Inc., Redmond, WA (US)

( * ) Notice: Subject to any disclaimer, the term of this patent is extended or adjusted under 35 U.S.C. 154(b) by 0 days.

(21) Appl. No.: 09/289,792

(22) Filed: Apr. 9, 1999

(51) Int. Cl.⁷ ................................................. A61B 5/00
(52) U.S. Cl. ........................ 600/331; 600/323; 600/322
(58) Field of Search ................. 600/309–311, 322–324, 600/331, 364, 365–366; 324/680, 610, 648, 651, 657, 666, 673, 706, 725; 439/620

(56) References Cited

U.S. PATENT DOCUMENTS

| | | | |
|---|---|---|---|
| 4,059,797 A | * 11/1977 | Gay | 324/680 |
| 4,856,530 A | * 8/1989 | Vandervelden | 600/505 |
| 5,184,059 A | * 2/1993 | Patino et al. | 320/125 |
| 5,654,712 A | * 8/1997 | Cheng | 341/155 |
| 5,660,567 A | * 8/1997 | Nierlich et al. | 439/620 |
| 5,720,293 A | * 2/1998 | Quinn et al. | 600/505 |
| 5,779,630 A | * 7/1998 | Fein et al. | 600/323 |
| 5,987,343 A | * 11/1999 | Kinast | 600/323 |
| 5,995,885 A | * 11/1999 | Kiani et al. | 600/310 |
| 5,997,343 A | * 12/1999 | Mills et al. | 439/489 |
| 6,064,899 A | * 5/2000 | Fein et al. | 600/323 |
| 6,351,658 B1 | * 2/2002 | Middleman et al. | 600/331 |

* cited by examiner

*Primary Examiner*—Eric F. Winakur
*Assistant Examiner*—Matthew Kremer
(74) *Attorney, Agent, or Firm*—Dorsey & Whitney LLP

(57) ABSTRACT

A system is described for identifying a cable transmitting a signal from a sensor to an electronic instrument. The cable includes a reactance element such as a capacitor or an inductor. The system identifies the cable by applying a voltage to a combination of a resistance and the reactance element to measure the reactance of the reactance element either alone or in combination with the resistance.

57 Claims, 6 Drawing Sheets

SYSTEM FOR IDENTIFYING A CABLE TRANSMITTING A SIGNAL FROM A SENSOR TO AN ELECTRONIC INSTRUMENT

TECHNICAL FIELD

The present invention relates generally to medical instruments, and more particularly, to a system for identifying a cable transmitting a signal from a sensor to an electronic instrument.

BACKGROUND OF THE INVENTION

Modem medical practice employs a wide variety of sensors for monitoring the condition of a patient during treatment, especially when the patient is undergoing a complex procedure such as surgery. For example, the patient's pulse rate, blood pressure, or the level of oxygen or carbon dioxide in the patient's blood may be monitored continuously by a sensor during a medical procedure.

A typical sensor is connected to an electronic instrument by a cable which transmits a signal from the sensor to the instrument to be processed and displayed on a continuous basis. For example, a conventional system for retrieving, processing, and displaying a signal from a sensor is shown in FIG. 1. A sensor 10 is connected to a cable 12 at a sensor terminal, and a connector 14 is attached adjacent to a signal terminal of the cable 12. The signal terminal may extend through the connector 14 or it may rest in a junction in the connector 14 which itself may transfer the signal. The cable 12 includes a signal conduit between the sensor terminal and the signal terminal which may be an electrically conductive material or an arrangement of optical fibers. The connector 14 is received by a receptacle 16 in an electronic instrument 18 such that the signal terminal and auxiliary terminals in the connector 14 are placed in electrical contact with circuitry inside the instrument 18. The connector 14 and the receptacle 16 may be joined by any suitable mechanical connection. The instrument 18 includes a display 19 for displaying a processed representation of the signal. The display 19 may be a tape display or a cathode ray tube or some other means of providing information. The system shown in FIG. 1 operates in the following manner. The sensor 10 generates a signal in response to a stimulus from a patient which is applied to the sensor terminal of the cable 12. The signal may be electrical or optical in nature. The signal is transferred by the signal conduit to the signal terminal of the cable 12, and then to the circuitry in the instrument 18 through the connector 14 and the receptacle 16. The signal is processed in the instrument 18 and presented in the display 19 according to methods appropriate for the particular signal.

As medical technology has improved, the number of sensors used to monitor a patient undergoing a procedure has increased substantially. Modem operating rooms are crisscrossed by cables, each cable transmitting a signal from an individual sensor which is monitoring a parameter of the patient. Each cable is attached to its own instrument which is adapted to process and display the signal provided by the cable and its sensor. It is of critical importance that the cables and sensors be matched correctly with their corresponding instruments. If two cables were to be accidentally switched to the wrong instruments then the information displayed by those instruments would be meaningless and potentially misleading. The chances for an incorrect connection increase in an emergency when there is little time to carefully consider each connection.

Another problem with medical monitors connect to a sensor is that various operating features or modes may be operational with some sensors but not operational with other sensors. In the past, these operating features or modes were often manually selected to correspond to the particular sensor connected to the monitor. However, manual selection of operating features or modes can be time-consuming, which is particularly disadvantageous in a medical emergency where time may be critical. Furthermore, manual selection of operating features or modes to correspond to a particular sensor is prone to errors because the wrong operating feature or mode may be selected for a particular sensor. For example, unique noise and artifact rejecting algorithms for use in a pulse oximetry monitor are disclosed in U.S. Pat. No. 5,687,722, 5,662,105, and 5,588,427 to Tien et al., all of which are incorporated herein by reference. In may not be necessary to use these noise and artifact rejecting features with some sensors, but it may be necessary to use these features with other sensors that are more sensitive to noise and artifact. If a noise and artifact sensitive sensor is connected to the monitor, but the operator mistakenly believes a less sensitive sensor is connected to the monitor, the operator may not enable the noise and artifact rejection features. Under these circumstances, the pulse oximetry monitor may fail to provide accurate indications of the oxygen saturation of a patient's blood.

The standardized production of cables increases the potential for an improper cable connection. Standardized cable designs lower manufacturing costs, but have the disadvantage that each cable has the same appearance, the same tactile characteristics, and the same terminal arrangements. When standardized cables are used for each sensor in an operating room, the absence of distinguishing features increases the likelihood that two or more cables will be connected to the wrong instruments.

A need exists for a system for distinguishing cables from each other in a medical environment such that the cables may be quickly and accurately connected to the proper instruments. Furthermore, it is desirable to prevent an instrument from processing and displaying a signal from the wrong sensor.

SUMMARY OF THE INVENTION

In accordance with the present invention, a system for identifying a cable transmitting a signal from a sensor to an electronic instrument is provided which permits a rapid identification of the cable. The cable includes an elongated signal conduit extending between a sensor terminal adapted to be connected to the sensor and a signal terminal. A connector is attached to the signal conduit adjacent to the signal terminal, and is attachable to the instrument to permit signal communication between the instrument and the sensor. A reactance element such as a capacitor or an inductor is coupled between two or more terminals of the connector which are coupled to the instrument. The reactance element as well as other cable identification components, may be packaged in the sensor, the sensor cable, and/or an adapter cable coupling the sensor to the instrument, as well as in connectors for those components. In one embodiment, the instrument includes a measurement circuit adapted to measure characteristics of the reactance element. In another embodiment, the instrument includes a microprocessor coupled to exchange signals with the measurement circuit. The microprocessor may also be coupled to the signal terminal to receive the signal from the sensor, and to generate information as a function of the signal. Various operating features or modes may be selected in the electronic instrument depending upon the nature of the cable and/or sensor connected to the cable, as determined by the characteristics of the reactance element.

In another embodiment, a method is provided for identifying a cable having a reactance element such as a capacitor or an inductor. A first voltage is provided to the reactance element, and a second voltage in the reactance element is monitored to detect a rate of change of the second voltage. The rate of change of the second voltage is compared to a predetermined rate and the cable is identified based on the comparison. In another embodiment, the reactance element is coupled to a bridge circuit and an alternating current signal is applied to the bridge circuit. An identification signal is generated when characteristics of the reactance element match predetermined characteristics.

DETAILED DESCRIPTION OF THE INVENTION

Several examples of a system for identifying a cable according to the invention are shown in FIGS. 2, 3, 6–9, 11, and 12. Each example is shown as an electrical schematic diagram of a microprocessor and a connector joined by a circuit which are part of a larger system for providing information based on a signal from a sensor. The larger system includes the sensor, a cable, the connector, and an electronic instrument having a receptacle to which the connector is removably attached. The instrument houses the circuit, the microprocessor, and a display. The external structure of the sensor, the cable, the receptacle, the instrument, and the display have not been shown in detail in order not to unnecessarily obscure the invention. It will be apparent to one skilled in the art that the schematic diagrams shown in FIGS. 2, 3, 6–9, 11, and 12 presuppose that the connector is mechanically attached to the receptacle such that terminals in the connector are electrically coupled to the circuit in the instrument.

Figure 1:
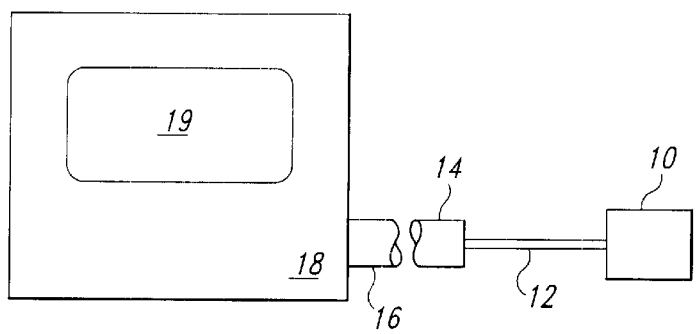
FIG. 1 is a side view of a sensor, a cable, and an electronic instrument according to the prior art.
Figure 2:
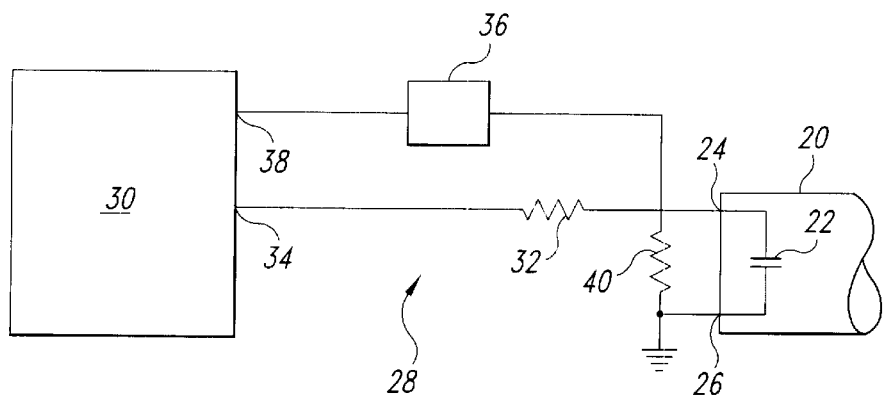
FIG. 2 is an electrical schematic diagram of a microprocessor and a connector with a capacitor joined by a resistive network and a trigger circuit according to the present invention.

A system for identifying a cable according to one embodiment of the invention is shown in FIG. 2. A connector 20 includes a capacitor 22 connected between two terminals 24 and 26. The terminals 24 and 26 are electrically coupled to adjoining terminals of a circuit 28 which includes a resistive network made up of two resistors 32 and 40 and a trigger circuit 36. A microprocessor 30 is coupled to the connector 20 through the circuit 28. The resistor 32 is coupled between the terminal 24 and a port 34 in the microprocessor 30. The trigger circuit 36, which may be a Shmitt trigger circuit, is coupled between a port 38 in the microprocessor 30 and the terminal 24. The resistor 40 is coupled between the terminals 24 and 26, and the terminal 26 is coupled to a ground voltage reference.

The capacitor 22 provides the connector 20 with a reactance having an RC time constant which is unique for the combination of the capacitor 22 and the resistors 32 and 40. The RC time constant governs a rate at which a voltage on the capacitor 22 changes when a voltage signal is applied to the combination of the capacitor 22 and the resistors 32 and 40. The connector 20 and a cable attached to it may be identified by the microprocessor 30 which determines the RC time constant by applying a voltage signal to the resistor 32 and monitoring the voltage on the capacitor 22.

Although the capacitor 22 is shown packaged in the connector 20, it will be understood that it may alternatively be packaged in a cable (not shown) or sensor (not shown) attached to the connector 20.

The connector 20 and a cable attached to it are identified in the following manner. A step function voltage signal or some other time-related voltage signal is provided by the microprocessor 30 from the port 34 to charge the capacitor 22 through the resistor 32 and the terminal 24. The voltage on the capacitor 22 is monitored at the terminal 24 by the trigger circuit 36 which provides a trigger signal to the port 38 when the voltage on the capacitor 22 reaches a predetermined threshold. The microprocessor 30 determines an elapsed time between the application of the step function voltage signal and the trigger signal. The elapsed time is governed by the RC time constant. The microprocessor 30 then compares the elapsed time with a predetermined value to identify the cable as being correct or incorrect. Once the cable is identified the microprocessor 30 terminates the step function voltage signal and the capacitor 22 discharges through the resistor 40 to the ground voltage reference. If the cable is identified as being the correct cable, then the microprocessor 30 may proceed to process a signal transmitted by the cable and send the results to a display. If the cable is identified as being incorrect, the microprocessor 30 may provide a message indicating such to the display.

In an alternative embodiment of the invention the capacitor 22 is discharged to determine the RC time constant. The microprocessor 30 provides a charging voltage from the port 34 to charge the capacitor 22 through the resistor 32 and the terminal 24. The capacitor 22 is charged to a selected voltage and the charging voltage is terminated. The capacitor 22 discharges through the resistor 40 to the ground voltage reference while the voltage on the capacitor 22 is monitored at the terminal 24 by the trigger circuit 36. The trigger circuit 36 provides a trigger signal to the port 38 when the voltage on the capacitor 22 falls below a threshold. The microprocessor 30 determines an elapsed time between the termination of the charging voltage and the trigger signal which is governed by the RC time constant. The microprocessor 30 then compares the elapsed time with a predetermined value to identify the cable as being correct or incorrect.

Figure 3:
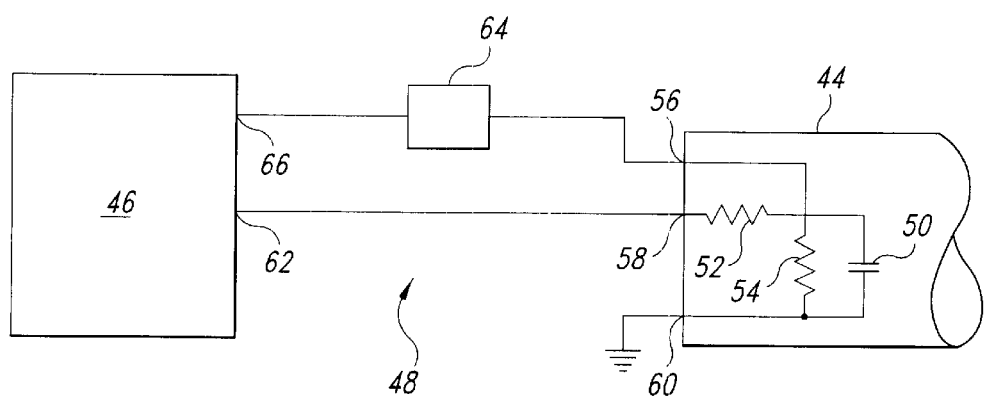
FIG. 3 is an electrical schematic diagram of a microprocessor and a connector with a capacitor and a resistive network, the microprocessor joined to the connector by a conductive coupling and a trigger circuit according to the present invention.

An alternative system for identifying a cable according to another embodiment of the invention is shown in FIG. 3. A connector 44 is coupled to a microprocessor 46 through a circuit 48. The connector 44 includes a capacitor 50 and two resistors 52 and 54 connected between three terminals 56, 58, and 60 which are electrically coupled to adjoining terminals of the circuit 48. The capacitor 50 and the resistor 54 are connected in parallel between the terminals 56 and 60, and the resistor 52 is connected between the terminals 56 and 58. The terminal 58 is coupled to a port 62 in the microprocessor 46, and a trigger circuit 64 is coupled between the terminal 56 and a port 66 in the microprocessor 46. The terminal 60 is coupled to a ground voltage reference. The system shown in FIG. 3 is similar to the system shown in FIG. 2 with the exception that a resistive network including the resistors 52 and 54 is located inside the connector 44 rather than between the connector 44 and the microprocessor 46. Furthermore, all or some of the resistors 52, 54 and the capacitor 50 may be packaged in a cable (not shown) or sensor (not shown) attached to the connector 44. The system shown in FIG. 3 identifies the connector 44 and a cable attached to it in a manner similar to the manner of identification described with respect to the system shown in FIG. 2.

Figures 4, 5:
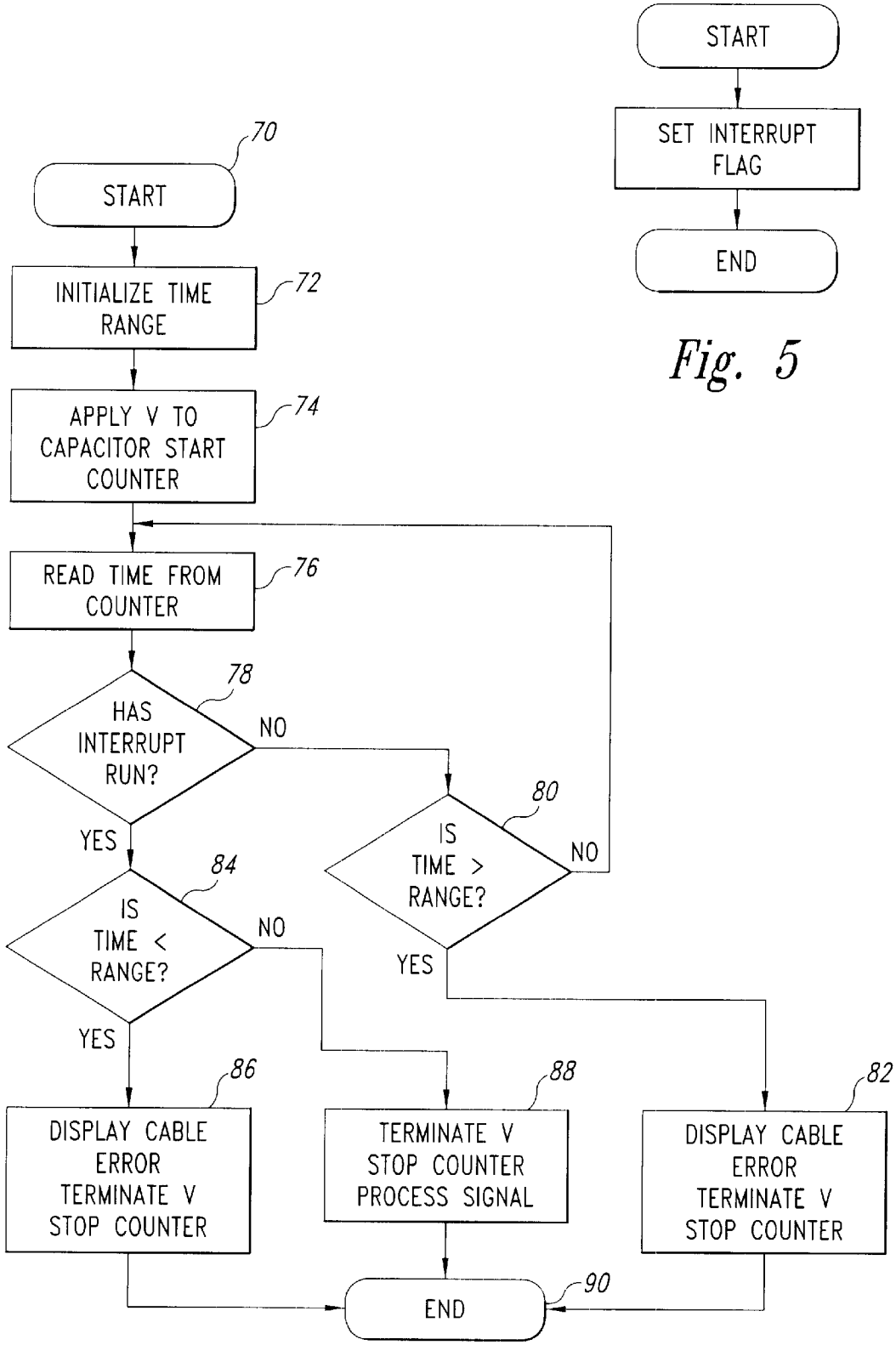
FIG. 4 is a flowchart of a software routine carried out by the microprocessor of FIG. 2 for identifying a cable and processing a signal from a sensor according to the present invention.
FIG. 5 is a flowchart of an interrupt routine carried out by the microprocessor of FIG. 2 in response to a signal from the trigger circuit according to the present invention.

FIG. 4 is a flowchart of a software routine carried out by the microprocessor 30 shown in FIG. 2 to identify the connector 20 and a cable attached to it. The microprocessor 30 identifies the cable according to the following steps. As the connector 20 is coupled to the circuit 28 the microprocessor 30 initiates the software routine with step 70. In step 72, the microprocessor 30 initializes a time range with which to identify the connector 20. In step 74, the microprocessor 30 applies a step function voltage signal from the port 34 to the capacitor 22 through the resistor 32 and the terminal 24 and simultaneously starts a counter.

The microprocessor 30 then executes a loop in the software routine beginning with step 76 until an interrupt routine occurs. A flowchart of the interrupt routine is shown in FIG. 5. According to the interrupt routine the microprocessor 30 sets a flag when the trigger signal is received from the trigger circuit 36 at the port 38. In other words, the flag is set when the voltage on the capacitor 22 reaches the threshold. Returning to step 76 in FIG. 4, the microprocessor 30 reads a time from the counter. In step 78, the microprocessor 30 determines whether the interrupt routine has been executed. If the interrupt routine has not been executed, the microprocessor 30 determines in step 80 whether the time read from the counter in step 76 is greater than the time range initialized in step 72. If the time read from the counter exceeds the time range, the cable is incorrect and the microprocessor 30 sends a cable error message to a display in step 82. The microprocessor 30 also terminates the step function voltage signal applied to the capacitor 22 and stops the counter in step 82. If the time read from the counter does not exceed the time range then the microprocessor 30 returns from step 80 to read the time from the counter in step 76.

If, in step 78, the microprocessor 30 determines that the interrupt routine has been executed, then the microprocessor 30 decides in step 84 whether the time read from the counter falls below the time range. If the time read from the counter is less than the time range, then the cable is incorrect and the microprocessor 30 sends a cable error message to the display in step 86. The microprocessor 30 also terminates the step function voltage signal applied to the capacitor 22 and stops the counter in step 86.

If, in step 84, the microprocessor 30 decides that the time read from the counter is within the time range, then the microprocessor 30 terminates the step function voltage signal applied to the capacitor 22 and stops the counter in step 88. The microprocessor 30 also processes a signal transmitted by the cable and sends the results to the display in step 88. The microprocessor 30 terminates the software routine in step 90 after either one of the steps 82, 86, or 88 have been executed.

Figure 6:
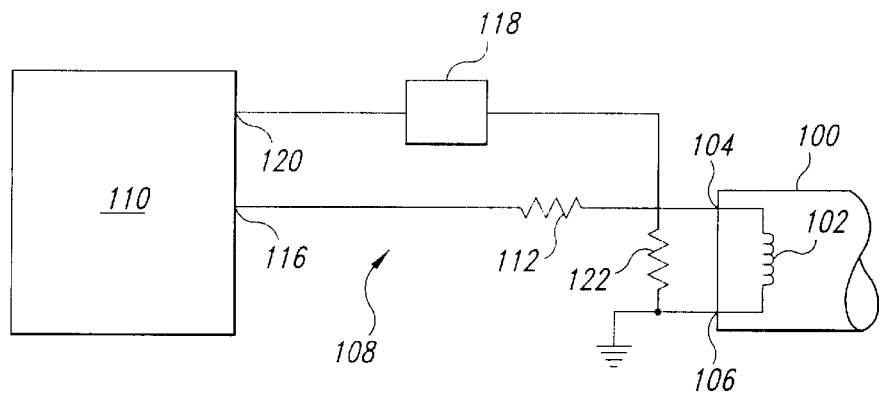
FIG. 6 is an electrical schematic diagram of a microprocessor and a connector with an inductor joined by a resistive network and a trigger circuit according to the present invention.

An alternative system for identifying a cable according to another embodiment of the invention is shown in FIG. 6. A connector 100 includes an inductor 102 connected between two terminals 104 and 106 which are electrically coupled to adjoining terminals of a circuit 108. A microprocessor is coupled to the connector 100 through the circuit 108. The circuit 108 includes a resistor 112 coupled between the terminal 104 and a port 116 in the microprocessor 110. A trigger circuit 118 is coupled between a port 120 of the microprocessor 110 and the terminal 104. A resistor 122 is coupled between the terminals 104 and 106 and the terminal 106 is coupled to a ground voltage reference. The system shown in FIG. 6 is similar to the system shown in FIG. 2 with the exception that the inductor 102 provides a reactance in the connector 100.

The connector 100 has an RL time constant which is unique for the combination of the inductor 102 and the resistors 112 and 122. The RL time constant governs a rate at which a voltage on the inductor 102 changes when a voltage signal is applied to the combination of the inductor 102 and the resistors 112 and 122. The connector 100 and a cable attached to it may be identified by the microprocessor 110 which determines the RL time constant by applying a voltage signal to the resistor 112 and monitoring the voltage on the inductor 102. Although the inductor 102 is shown packaged in the connector 100, it may alternatively be packaged in a cable (not shown) or sensor (not shown) attached to the connector 100.

The connector 100 and a cable attached to it are identified in the following manner. A step function voltage signal is provided by the microprocessor 110 from the port 116 to charge the inductor 102 through the resistor 112 and the terminal 104. A voltage on the inductor 102 is monitored at the terminal 104 by the trigger circuit 118, and decreases as a current in the inductor 102 rises in response to the application of the step function voltage signal. When the voltage at the terminal 104 is reduced below a threshold, the trigger circuit 118 provides a trigger signal to the port 120. The microprocessor 110 determines an elapsed time between the application of the step function voltage signal and the trigger signal which is governed by the RL time constant. The microprocessor 110 then compares the elapsed time with a predetermined value to identify the cable as being correct or incorrect. Once the cable is identified the microprocessor 110 terminates the step function voltage signal and the inductor 102 discharges through the resistor 122.

Figure 7:
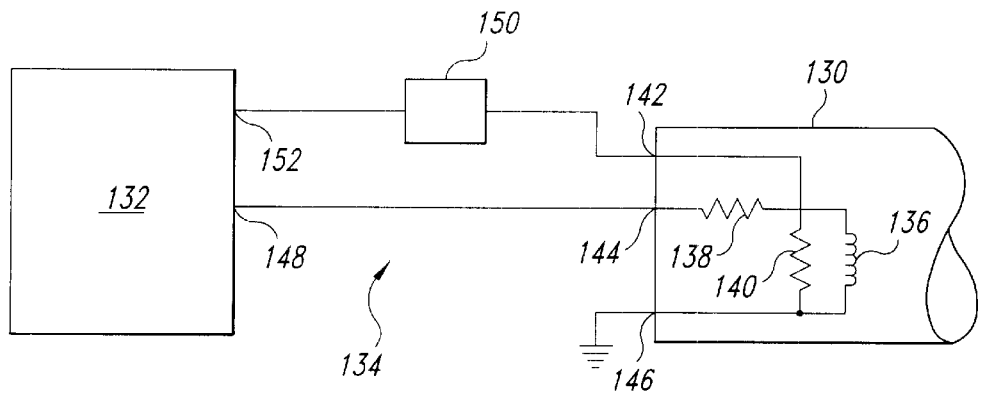
FIG. 7 is an electrical schematic diagram of a microprocessor and a connector with an inductor and a resistive network, the microprocessor joined to the connector by a conductive coupling and a trigger circuit according to the present invention.

An alternative system for identifying a cable according to another embodiment of the invention is shown in FIG. 7. A connector 130 is coupled to a microprocessor 132 through a circuit 134. The connector 130 includes an inductor 136 and two resistors 138 and 140 connected between three terminals 142, 144, and 146 which are electrically coupled to adjoining terminals of the circuit 134. The inductor 136 and the resistor 140 are connected in parallel between the terminals 142 and 146, and the resistor 138 is connected between the terminals 142 and 144. The terminal 144 is coupled to a port 148 in the microprocessor 132, and a trigger circuit 150 is coupled between the terminal 142 and a port 152 in the microprocessor 132. The terminal 146 is coupled to a ground voltage reference. The system shown in FIG. 7 is similar to the system shown in FIG. 6 with the exception that a resistive network including the resistors 138 and 140 is located inside the connector 130 rather than between the connector 130 and the microprocessor 132. The resistors 138 and 140 and the inductor 136 may alternatively be packaged in or distributed throughout a cable (not shown) or sensor (not shown) coupled to the connector 130.

The system shown in FIG. 7 identifies the connector 130 and a cable attached to it in a manner similar to the manner of identification described with respect to the system shown in FIG. 6.

Figure 8:
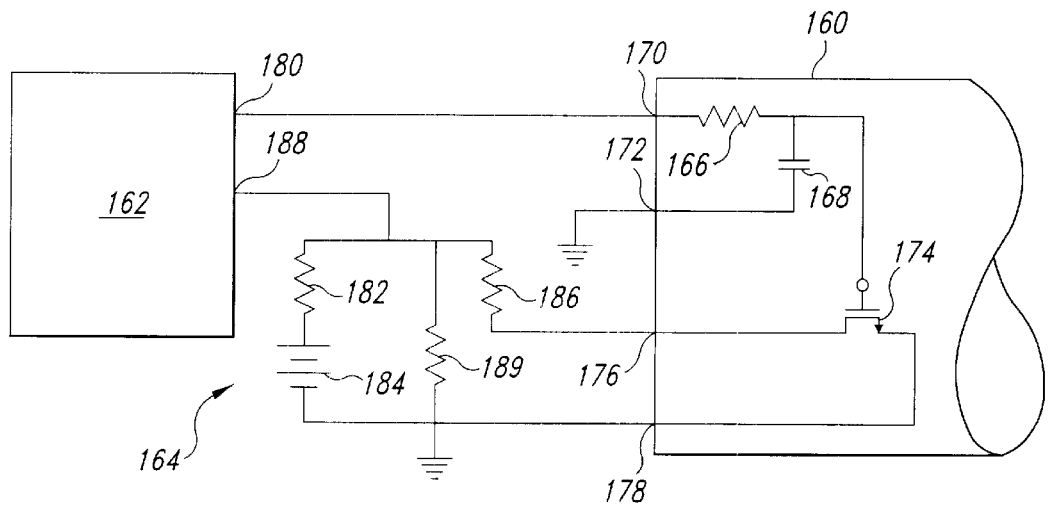
FIG. 8 is an electrical schematic diagram of a microprocessor and a connector with a capacitor, a resistor, and a switch, the microprocessor joined to the connector by a conductive coupling and a current detection circuit according to the present invention.

An alternative system for identifying a cable according to still another embodiment of the invention is shown in FIG. 8. A connector 160 is coupled to a microprocessor 162 through a circuit 164. The connector includes a resistor 166 and a capacitor 168 connected in series between two terminals 170 and 172 which are electrically coupled to adjoining terminals in the circuit 164. An N-channel MOS transistor 174 is connected between two terminals 176 and 178 which are also electrically coupled to adjoining terminals in the circuit 164. A control terminal of the transistor 174 is connected to a node between the resistor 166 and the capacitor 168 such that a voltage on the capacitor 168 is applied to the control terminal. The terminal 170 is coupled to a port 180 in the microprocessor 162, and the terminal 172 is coupled to a ground voltage reference. The parallel combination of a resistor 189 and a resistor 182 and a voltage source 184 connected in series are connected in series with a resistor 186 and the transistor 174, which is connected between the terminal 176 and the terminal 178. The junction between the resistor 182 and the resistor 186 is connected to a port 188 in the microprocessor 162. The transistor 174 is used as a switch to control current in a circuit including the transistor 174, the resistor 182, the resistor 189, the voltage source 184, and the resistor 186. The transistor 174 is rendered conductive when the voltage on the capacitor 168 exceeds a threshold. The voltage at the junction between the resistor 182, 186 changes when the transistor 174 is rendered conductive, and this change is detected by the microprocessor 162 through the port 188. Those skilled in the art will understand that another type of transistor such as BJT, a JFET or an analog switch may be substituted for the transistor 174. Also, the resistor 189 may be omitted from the circuit 164 without substantially affecting its operation. As with the previously described embodiments, the above-described cable identification components may be packaged in or distributed throughout a cable (not shown) or sensor (not shown) coupled to the connector 160. The connector 160 and a cable attached to it are identified in the following manner. A step function voltage signal is provided by the microprocessor 162 from the port 180 to charge the capacitor 168 through the terminal 170 and the resistor 166. The voltage on the capacitor 168 rises according to an RC time constant based on the capacitor 168 and the resistor 166, and as it rises above the threshold, the transistor 174 is rendered conductive. The change in voltage at the node between resistors 182, 186 is then detected by the microprocessor 162. The microprocessor 162 determines an elapsed time between the application of the step function voltage signal and the change in voltage, which is governed by the RC time constant. The microprocessor 162 then compares the elapsed time with a predetermined value to identify the cable as being correct or incorrect.

Figure 9:
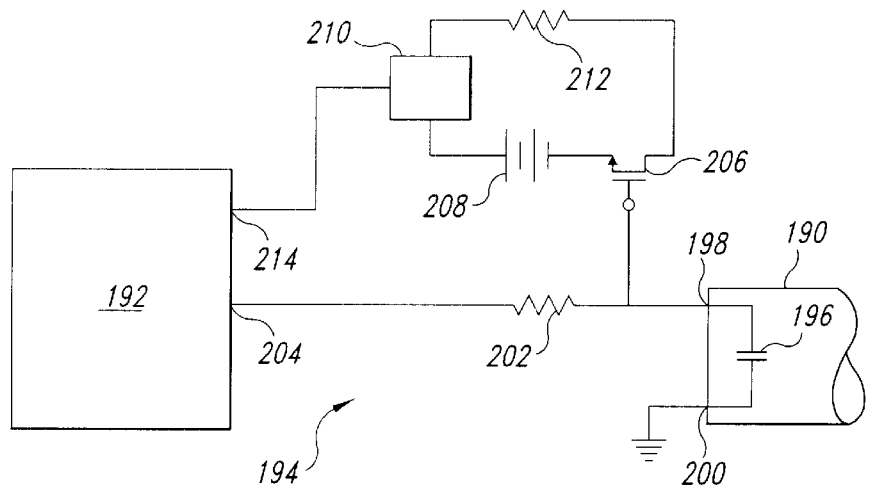
FIG. 9 is an electrical schematic diagram of a microprocessor and a connector with a capacitor joined by a resistive coupling and a voltage detection circuit according to the present invention.

An alternative system for identifying a cable according to another embodiment of the invention is shown in FIG. 9. A connector 190 is shown coupled to a microprocessor 192 through a circuit 194. The connector 190 includes a capacitor 196 connected between two terminals 198 and 200 which are electrically coupled to adjoining terminals in the circuit 194. A resistor 202 is coupled between the terminal 198 and a port 204 in the microprocessor 192. The terminal 200 is coupled to a ground voltage reference. The terminal 198 is coupled to a control terminal of an N-channel MOS transistor 206 which is connected in series with a voltage source 208, a current detection circuit 210, and a resistor 212. An output of the current detection circuit 210 is connected to provide a trigger signal to a port 214 in the microprocessor 192. Those skilled in the art will understand that an analog switch or another type of transistor, such as a BJT or a JFET, may be substituted for the transistor 206.

The system shown in FIG. 9 is similar to the system shown in FIG. 8 with the exception that the transistor 206 is located in the circuit 194 rather than in the connector 190. The capacitor may, of course, be located either in a cable (not shown) or a sensor (not shown) coupled to the connector 190. The system shown in FIG. 9 identifies the connector 190 and a cable attached to it in a manner similar to the manner of identification described with respect to the system shown in FIG. 8.

Figure 10:
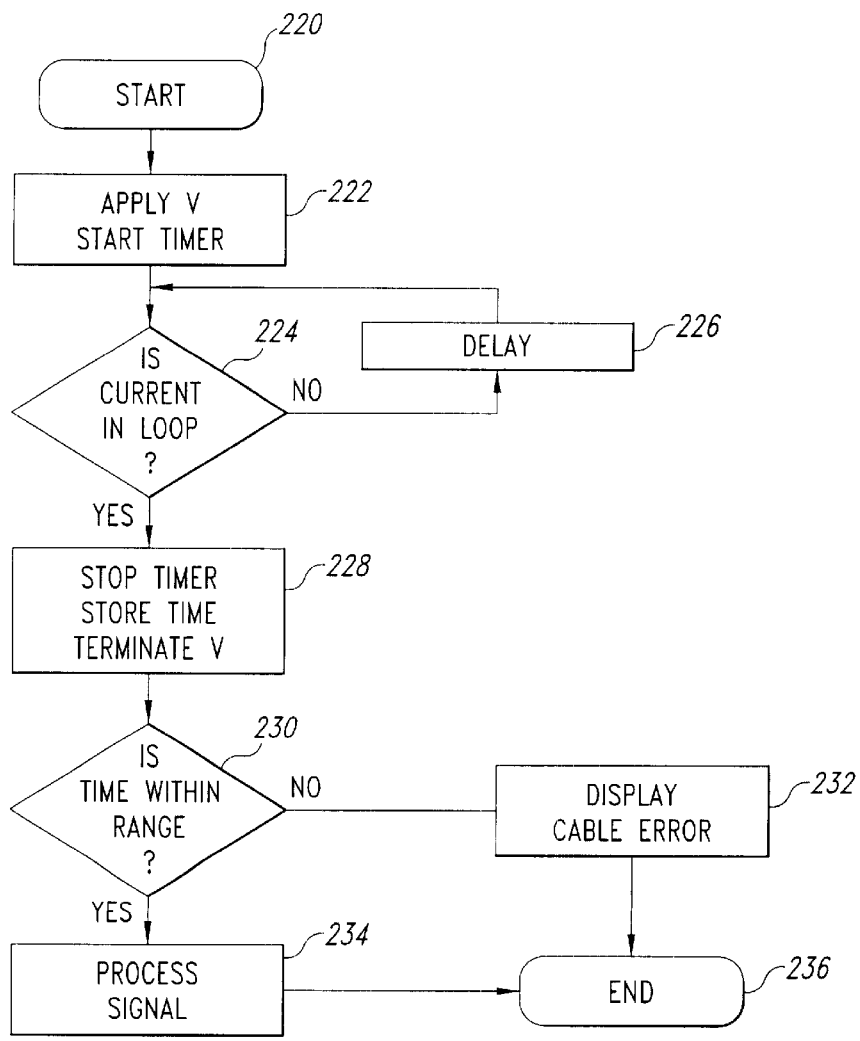
FIG. 10 is a flowchart of a software routine carried out by the microprocessor of FIG. 9 for identifying a cable and processing a signal from a sensor according to the present invention.

FIG. 10 is a flowchart of a software routine carried out by the microprocessors 162 or 192 of FIGS. 8 or 9, respectively, to identify the connector and a cable attached to it. The microprocessor 192 initiates the software routine in step 220 when the connector 190 is coupled to the circuit 194.

The microprocessor 192 applies a step function voltage signal to the capacitor 196 through the resistor 202 and the terminal 198 and starts a timer in step 222.

The microprocessor 192 executes a loop in the software routine including steps 224 and 226 until current is detected by the current detection circuit 210 and the trigger signal is provided to the port 214. The microprocessor 192 determines whether the trigger signal has been received in step 224, and if it has not, a delay step 226 is executed before the microprocessor 192 returns to step 224. If current is detected by the current detection circuit 210 then the microprocessor 192 stops the timer, stores the time accumulated by the timer, and terminates the step function voltage signal in step 228. In step 230, the microprocessor 192 determines whether the stored time is within a range which indicates that the connector 190 and the cable attached to it are correctly identified. If the stored time is not within the range then the microprocessor 192 sends a cable error message to a display in step 232. If the stored time is within the range then the microprocessor 192 processes a signal transmitted by the cable and sends the results to a display in step 234. When either step 232 or 234 has been executed, the microprocessor 192 terminates the software routine in step 236.

Figure 11:
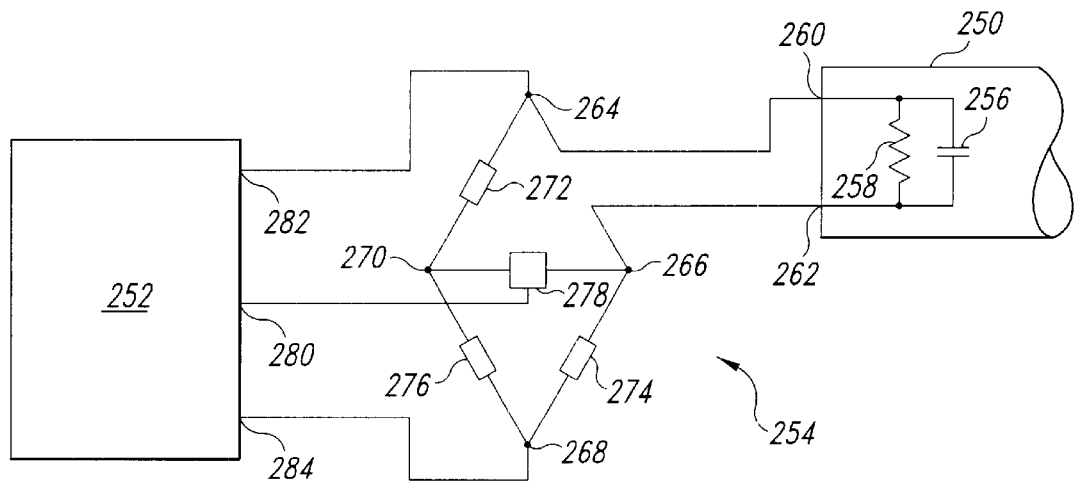
FIG. 11 is an electrical schematic diagram of a microprocessor and a connector with a capacitor and a resistor, the microprocessor joined to the connector by a bridge circuit according to the present invention.

An alternative system for identifying a cable according to a further embodiment of the invention is shown in FIG. 11. A connector 250 is shown coupled to a microprocessor 252 through a bridge circuit 254. The connector 250 includes a capacitor 256 and a resistor 258 connected in parallel between two terminals 260 and 262 which are electrically coupled to adjoining terminals in the bridge circuit 254. The bridge circuit 254 includes three impedance elements and a detection circuit connected between four nodes 264, 266, 268, and 270. A first impedance element 272 is connected between the nodes 264 and 270, a second impedance element 274 is connected between the nodes 266 and 268, and a third impedance element 276 is connected between the nodes 268 and 270. The terminals 260 and 262 are coupled to the nodes 264 and 266, respectively. A detection circuit 278 is connected between the nodes 266 and 270, and has an output connected to a port 280 of the microprocessor 252. The detection circuit 278 provides a null signal to the microprocessor 252 through the port 280 when a null condition exists between the nodes 266 and 270. The node 264 is connected to a port 282 of the microprocessor 252, and the node 268 is connected to a port 284 of the microprocessor 252. Either the resistor 258 or the capacitor 256, but not both, may be removed from the connector 250 and made a part of the bridge circuit 254. Alternatively, some or all of the components of the bridge circuit 254 may be located in either or both of a cable (not shown) or sensor (not shown) coupled to the connector 250.

The system shown in FIG. 11 identifies the connector 250 and a cable attached to it in the following manner. The microprocessor 252 applies an alternating current signal between the nodes 264 and 268 of the bridge circuit 254 through the ports 282 and 284. If the impedance provided by the capacitor 256 and the resistor 258 in the connector 250 is the correct impedance then the bridge circuit 254 is in balance and the detection circuit 278 will register a null condition with a null signal provided to the port 280 of the microprocessor 252. If the impedance is incorrect then the null signal will not be generated and, after a selected period of time, the microprocessor 252 will send a cable error message to a display. If the connector 250 is identified as being correct, the microprocessor 252 processes a signal transmitted by the cable and sends the results to the display.

Those skilled in the art will recognize that there exists a wide variety of bridge circuits for evaluating different types of impedances. As a consequence, the particular arrangement of the capacitor 256 and the resistor 258 in the connector 250 may be replaced by any combination of resistors and a capacitor or an inductor provided that the bridge circuit 254 is suitably modified to evaluate the impedance. Also, other means may be used in place of the trigger circuit in the embodiments of FIGS. 2–3 and 6–7 to detect a predetermined voltage level. For example, a voltage comparator may be used. Also, a time related characteristic of the reactance circuit may be measured by means other than detecting a predetermined voltage. For example, a differentiator may be used to directly measure the rate of change of a voltage on the reactance circuit. Finally, a stimulus signal other than a step function, such as a voltage ramp, may be used.

Figure 12:
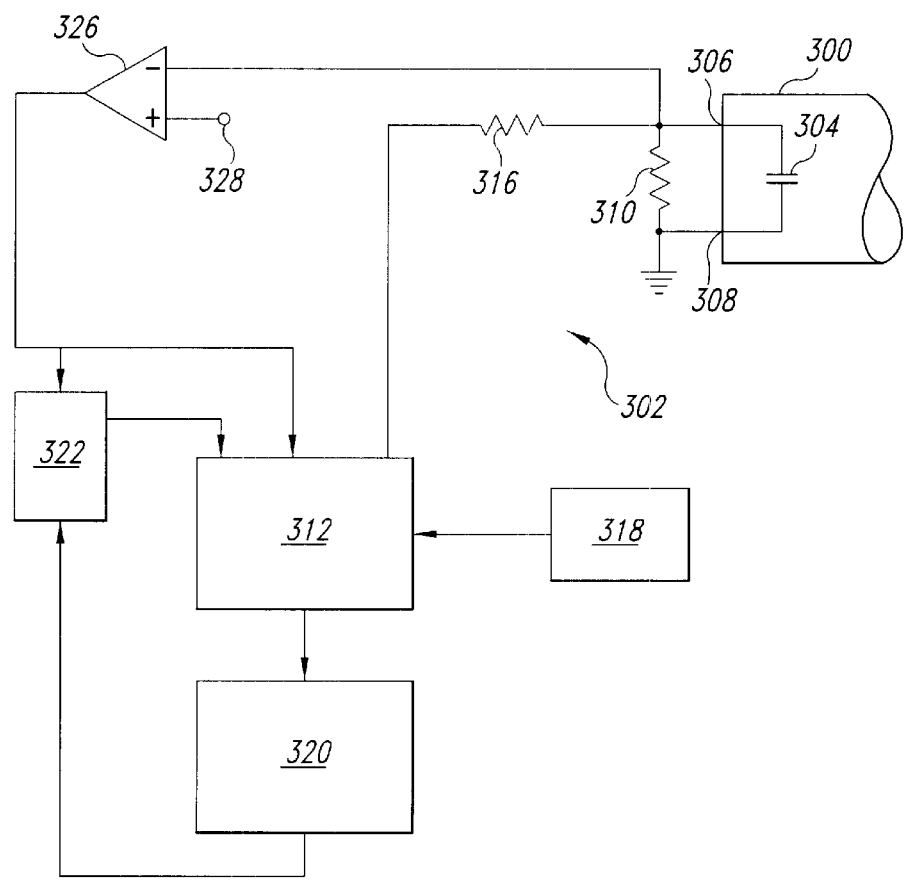
FIG. 12 is an electrical schematic diagram of a connector with a capacitor coupled to a circuit for determining a rate of change of voltage across the capacitor according to the present invention.

An alternative system for identifying a cable according to a further embodiment of the invention is shown in FIG. 12. A connector 300 is coupled to a circuit 302 for identifying the connector 300 and a cable attached to it. The connector 300 includes a capacitor 304 connected between two terminals 306 and 308 which are electrically coupled to adjoining terminals in the circuit 302. The circuit 302 includes the following elements. A resistor 310 is coupled between the terminals 306 and 308, and the terminal 308 is coupled to a ground voltage reference. A control logic circuit 312 includes an output which is coupled through a resistor 316 to the terminal 306, and an input for receiving a control signal from a microprocessor 322. The control logic circuit 312 receives a clock signal from a clock signal source 318, and provides a control signal to a counter 320. The counter 320 includes an output connected to the microprocessor 322.

The terminal 306 is also coupled to an inverting input of a comparator 326. A non-inverting input of the comparator 326 is connected to a reference voltage 328, and an output of the comparator 326 is provided to the microprocessor 322 and to an input of the control logic circuit 312. As with the embodiment of FIG. 11, some or all of the components of the circuit 302 may be located in either or both of a cable (not shown) or sensor (not shown) coupled to the connector 300. The system shown in FIG. 12 identifies the connector 300 and a cable attached to it in the following manner. The control logic circuit 312 receives a start signal from the microprocessor 322 and in response starts the counter 320 and provides a charging voltage to charge the capacitor 304 through the resistor 316 and the terminal 306. A voltage on the capacitor 304 is monitored by the comparator 326 through the terminal 306. The comparator 326 outputs a high signal to the microprocessor 322 and the control logic circuit 312 while the voltage on the capacitor 304 is less than the reference voltage 328. As the voltage on the capacitor 304 rises above the reference voltage 328, the output of the comparator 326 switches to a low signal which indicates to the microprocessor 322 and the control logic circuit 312 that the voltage on the capacitor 304 has reached a threshold. At this point, the control logic circuit 312 terminates the charging voltage provided to the capacitor 304 and stops the counter 320. The microprocessor 322 may identify the cable by determining an RC time constant for the capacitor 304 and the resistors 310 and 316 according to the count provided by the counter 320 which indicates an elapsed time between the application of the charging voltage and the low signal received from the comparator 326. Once the charging voltage is terminated the capacitor is discharged through the resistor 310 and the ground voltage reference.

Figure 13:
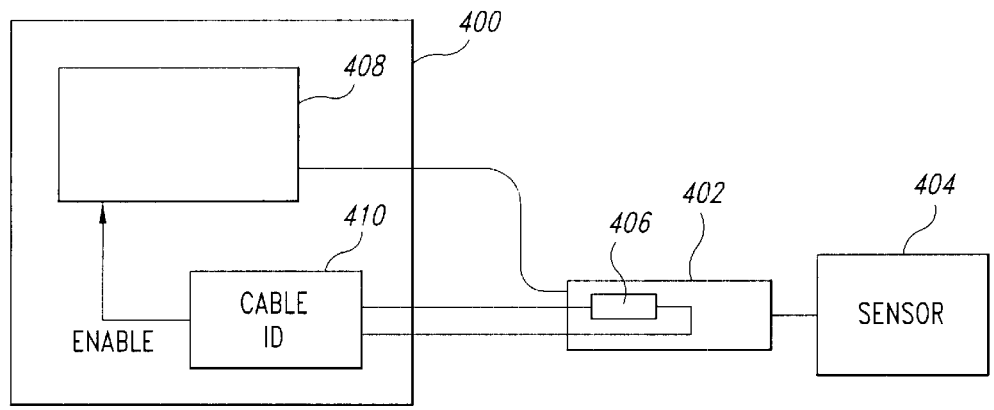
FIG. 13 is a block diagram of a monitoring system including a monitor connected to a sensor through a cable in which an operating feature or mode is enabled as a function of the identity of the cable and/or sensor.

The various embodiments of a cable and/or sensor identification system in accordance with the invention may be used to enable or select an operating feature or mode of an electronic instrument to which the cable is connected. With reference to FIG. 13, an electronic instrument 400 is coupled through a cable 402 to a sensor 404. The sensor 404 may be a conventional pulse oximetry sensor, and the cable 402 may be of conventional design except that either the cable 402 or the sensor 404 contains a reactance element 406 and possibly other components, as described above with reference to FIGS. 2–12. The electronic instrument 400 may be a pulse oximetry monitor, although it may monitor other physiological parameters when used with appropriate sensors other than the pulse oximetry sensor 404. In addition to conventional components 408 of the instrument 400, the instrument 400 also includes cable identifying circuitry 410 in accordance with one of the embodiments of the invention described above. The cable identifying circuitry 410 provides an ENABLE signal that is used in the electronic instrument 400 to enable or select one or more operating features or modes of the conventional components 408. In the embodiment shown in FIG. 13, the ENABLE signal enables one or more of the artifact or noise rejecting algorithms described in the above-cited patents to Tien et al. In this manner, the operating features or modes of the electronic instrument 400 can be automatically enabled or selected depending upon a characteristic of the cable 402 or the sensor 404 connected to the cable 402 as identified by signals from the reactance element 406.

As mentioned in connection with the various embodiments of the invention described above, the reactive components and other circuitry may be included in the connectors for the sensor or the sensor cable. Some of these cable identification components may also be included in an electronic device, such as a monitor, to which the sensor cable is connected. However, in a broader sense, the reactive components and other circuitry may be packaged in other configurations, as shown in FIGS. 14 and 15.

Figure 14:
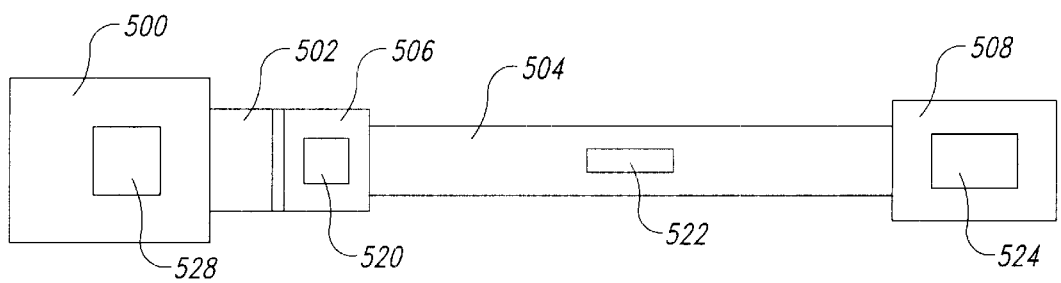
FIG. 14 is a block diagram of a monitoring system including a monitor connected to a sensor through a sensor cable showing the various locations in which reactive components and other cable identification components may be packaged.
Figure 15:
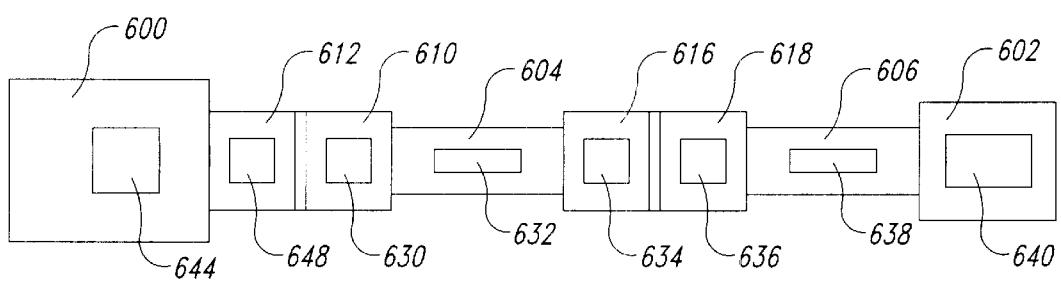
FIG. 15 is a block diagram of a monitoring system including a monitor connected to a sensor through a sensor cable and an adapter cable showing the various locations in which reactive components and other cable identification components may be packaged.

With reference to FIG. 14, an electronic instrument 500, such as a pulse oximetry monitor, includes an instrument connector 502 that is coupled to a sensor cable 504 through a sensor cable connector 506. The opposite end of the sensor cable 504 is connected to a sensor 508, such as a pulse oximetry sensor. However, it will be understood that the sensor 508 may be detachably coupled to the sensor cable 504 through a connector (not shown) or the like. One or more reactive components, such as a capacitor or an inductor, as well a other cable identification components, are included in one or more of the following locations: as circuitry 520 in the sensor connector 506, circuitry 522 in the sensor cable 504, and/or circuitry 524 in the sensor 508. Some, but not all, of the reactive components and other circuitry may also be included as circuitry 528 in the instrument 500 or the instrument connector 502. The only requirement is that one or more of these cable identification components must be included in the sensor cable 504, sensor connector 506, or sensor 508 so that the instrument 500 can identity the cable 504, connector 506, or sensor 508.

Although a single cable 504 is shown in FIG. 14 coupling the instrument 500 to the sensor 508, other configurations may be used. For example, as illustrated in FIG. 15, an electronic instrument 600 is coupled to a sensor 602 through an adapter cable 604 and a sensor cable 606. The adapter cable 604 includes a first adapter connector 610 coupled to an instrument connector 612, and a second adapter connector 616 coupled to a sensor connector 618. One or more reactive components and other cable identification components are included in one or more of the following locations: as circuitry 630 in the first adapter connector 610, circuitry 632 in the adapter cable 604, circuitry 634 in the second adapter connector 616, circuitry 636 in the sensor connector 618, circuitry 638 in the sensor cable 606, and/or circuitry 540 in the sensor 602. Some, but not all, of the reactive components and other circuitry may also be included in circuitry 644 in the instrument 600 and/or circuitry 648 in the instrument connector 612. The only requirement is that one or more of these cable identification components must be included in a location other than the instrument 600 and connector 612 so that the instrument 600 can identify the adapter cable 604 and/or the sensor cable 606 and sensor 602.

In one embodiment, the sensor connector 618, sensor cable 606, and sensor 602 do not contain any of the cable identification components described above. Instead, the sensor 602 and its associated cable 606 and connector 618 are available from a variety of sources. However, the sensor 602 can still be identified by the instrument 600 because the adapter connector 616 is specifically adapted to mate with the sensor connector 618, and the adapter cable 604, the connector 610, and/or the connector 616 contain one or more reactive components and possibly other circuitry that may be identified by the instrument 600. Various other combinations may, of course, also be used.

Although several embodiments of the invention have been described above for purposes of illustration, various modifications may be made without deviating from the spirit and scope of the invention For example, as mentioned above, the resistors which provide a resistance for the RC time constant for a connector may be located within the connector or in a circuit coupled to the connector. Also, as also mentioned above, the reactance element can be physically located at the sensor and coupled to the connector through the cable. Numerous variations are well within the scope of this invention. Accordingly, the invention is not limited except as by the appended claims.

What is claimed is:

1. A cable for connecting a sensor to an electronic instrument, comprising:

an elongated signal conduit extending between a sensor terminal adapted for connection to the sensor and a signal terminal;

a connector attached to the signal conduit adjacent the signal terminal, the connector being attachable to the instrument to permit signal communication between the instrument and the sensor through the connector, the signal conduit, and the sensor terminal; and a reactance element coupled to at least one resistor to form a network having a predetermined time constant, the network being coupled to the instrument through a plurality of terminals of the connector, the instrument being configured to apply a signal to the network having a single polarity, and to measure a corresponding response in the network that is a function of a predetermined time constant.

2. The cable of claim 1 wherein the elongated signal conduit is comprised of one or more conductive wires.

3. The cable of claim 1 wherein the elongated signal conduit is comprised of one or more optical fibers.

4. The cable of claim 1 wherein the reactance element is mounted in the connector.

5. The cable of claim 1 wherein the reactance element is mounted in the signal conduit.

6. The cable of claim 1 wherein the signal conduit comprises:

a sensor cable adapted for coupling to a sensor at one end and to a sensor connector at the other end; and an adapter cable adapted for coupling to the connector at one end and to the sensor connector at the other end.

7. The cable of claim 6 wherein the reactance element is mounted in the adapter cable.

8. The cable of claim 6 wherein the reactance element is mounted in the sensor cable.

9. The cable of claim 1 wherein the reactance element is a capacitor.

10. The cable of claim 1 wherein the reactance element is an inductor.

11. The cable of claim 1, further comprising a switch having one of two states wherein the state of the switch changes over a selected time interval in response to a signal from the reactance element, the time interval being a function of the predetermined time constant.

12. A connector for joining a cable to an electronic instrument, the cable transmitting a signal to the instrument, the connector comprising:
    a connector body attached to an end of the cable;
    a plurality of terminals in the connector body adapted to be coupled to the instrument; and
    a reactance element coupled to at least one resistor to form a network having a predetermined time constant, the network being positioned in the connector body and coupled between the terminals, the instrument being operable to apply a signal to the network and operable to measure a corresponding response in the network, the response being a function of the predetermined time constant.

13. The connector of claim 12 wherein the reactance element is a capacitor.

14. The connector of claim 12 wherein the reactance element is an inductor.

15. The connector of claim 12, further comprising a switch having one of two states wherein the state of the switch changes in response to a signal from the reactance element over a selected time interval, the time interval being a function of the predetermined time constant.

16. A system for providing information based on a sensor signal from a sensor, comprising:
    a cable including an elongated signal conduit adapted for coupling to a sensor at one end and to a signal terminal at the other end, the elongated signal conduit adapted for coupling a sensor signal from the sensor terminal to the signal terminal;
    a connector attached to the cable adjacent to the signal terminal, the connector having a plurality of terminals;
    a reactance element coupled to at least one resistor to form a network having predetermined reactance characteristics that is coupled between selected terminals of the connector; and
    an electronic instrument coupled to the terminals in the connector, the instrument being adapted to provide the information as a function of the sensor signal and to apply a signal to the network having a single polarity to identify the cable based on a measurement of a selected time interval, the time interval being a function of the predetermined reactance characteristics of the network.

17. The system of claim 16 wherein the reactance element is a capacitor.

18. The system of claim 16 wherein the reactance element is an inductor.

19. The system of claim 16 wherein the instrument comprises:
    a microprocessor coupled to one or more of the terminals in the connector to receive the sensor signal, the microprocessor being adapted to provide the information as a function of the sensor signal;
    a display coupled to the microprocessor to receive and display the information; and
    a measurement circuit coupled to exchange signals with the microprocessor, the measurement circuit being coupled to receive the selected ones of the terminals in the connector so that the measurement circuit is adapted to measure a selected time interval, the time interval being a function of the predetermined reactance characteristics of the network and determined in response to a command signal from the microprocessor.

20. The system of claim 19 wherein the measurement circuit comprises:
    a first circuit coupled between the microprocessor and the selected ones of the terminals in the connector to provide a voltage having a single polarity from the microprocessor to the network, the microprocessor applying the voltage to the network and interrupting the voltage at a first time; and
    a trigger circuit for sensing a voltage in the reactance network, the trigger circuit supplying a trigger signal to the microprocessor when the voltage in the reactance element equals a threshold voltage at a second time, the difference between the first time and the second time being the selected time interval.

21. The system of claim 19, further comprising:
    a switch coupled between a plurality of terminals in the connector having one of two states wherein the state of the switch changes over the selected time interval in response to a signal from the reactance network, the time interval being a function of the selected reactance characteristics.

22. The system of claim 21 wherein the measurement circuit comprises:
    a conductive coupling between the microprocessor and the reactance element adapted to provide a first voltage from the microprocessor to the reactance element; and
    a voltage source and a current detector coupled in series with the switch through the terminals in the connector, the current detector providing a detection signal to the microprocessor when the state of the switch changes.

23. The system of claim 19 wherein the measurement circuit comprises:
    a conductive coupling between the microprocessor and the reactance element adapted to provide a first voltage from the microprocessor to the reactance element;
    a switch having one of two states wherein the state of the switch changes over a selected time interval in response to a signal from the network, the time interval being a function of the selected reactance characteristics of the network; and
    a voltage source and a current detector coupled in series with the switch, the current detector providing a detection signal to the microprocessor when the state of the switch changes.

24. The system of claim 16 wherein the network is mounted in the connector.

25. The system of claim 16 wherein the network is mounted in the cable.

26. The system of claim 16 further comprising a sensor coupled to the cable, and wherein the network is mounted in the sensor.

27. The system of claim 16 wherein the electronic instrument further includes an operating feature or mode that is enabled by an enable signal, and wherein the electronic instrument is constructed to generate the enable signal as a function of the identification of the cable.

28. The system of claim 27 wherein the electronic instrument comprises a pulse oximetry monitor.

29. The system of claim 28 wherein the feature of the pulse oximetry monitor enabled by the enable signal is a noise or artifact rejecting algorithm.

30. The system of claim 29 wherein the feature enabled by the enable signal is a noise or artifact rejecting algorithm.

31. The system of claim 28 wherein the cable comprises:
a sensor cable adapted for coupling to the sensor at one end and to a sensor connector at the other end; and
an adapter cable adapted for coupling to the connector at one end and to the sensor connector at the other end.

32. The system of claim 16 wherein the network is mounted in the adapter cable.

33. The system of claim 31 wherein the network is mounted in the sensor cable.

34. The system of claim 31 wherein the network is mounted in the sensor connector.

35. A method for identifying a cable having a reactance network with selected reactance characteristics, the method comprising the steps of
providing a first voltage to the network, wherein the first voltage has a single polarity;
monitoring a second voltage in the network to detect a rate of change of the second voltage; and
comparing the rate of change of the second voltage to a predetermined rate and identifying the cable based on the comparison.

36. The method of claim 29 wherein the step of providing a first voltage to the network comprises the step of providing a first voltage to a capacitor.

37. The method of claim 29 wherein the step of providing a first voltage to the network comprises the step of providing a first voltage to a resistor coupled to a capacitor.

38. The method of claim 29 wherein the step of providing a first voltage to the network reactance element comprises the step of providing a first voltage to an inductor.

39. The method of claim 29 wherein the step of providing a first voltage to the network comprises the step of providing a first voltage to a resistor coupled to an inductor.

40. The method of claim 29 wherein the step of monitoring a second voltage in the network comprises the steps of:
coupling the second voltage to a switch to control a state of the switch;
detecting when the state of the switch changes; and
determining a time interval between the step of providing a first voltage and the detection of the changed state of the switch.

41. The method of claim 40 wherein the step of detecting when the state of the switch changes comprises the steps of:
applying a voltage to a circuit coupled to the switch; and
detecting a change in current in the circuit when the state of the switch changes.

42. A method for identifying a cable having an inductor coupled to a resistor to form a network having selected reactance characteristics, the method comprising the steps of:
coupling the network to a bridge circuit;
applying an alternating current signal to the bridge circuit; and
generating an identification signal when the reactance characteristics of the network match predetermined reactance characteristics.

43. A method for analyzing a sensor signal generated by a sensor and transmitted by a cable, the cable having a reactance element with selected reactance characteristics, the method comprising the steps of:
coupling the cable to an electronic instrument such that the instrument receives the sensor signal;
providing a first voltage to the reactance element the first voltage having a single polarity;
monitoring a second voltage in the reactance element to detect a rate of change of the second voltage;
comparing the rate of change of the second voltage to a predetermined rate and identifying the cable based on the comparison; and
analyzing the sensor signal in the instrument based on the identification of the cable.

44. The method of claim 43 wherein the step of coupling the cable comprises the step of coupling the cable to an electronic instrument having a microprocessor such that the microprocessor receives the sensor signal.

45. The method of claim 44 wherein the step of monitoring a second voltage comprises the step of monitoring a second voltage in the reactance element with a software routine carried out in the microprocessor.

46. The method of claim 45 wherein the step of comparing the rate of change comprises the steps of:
generating a trigger signal when the second voltage equals a threshold voltage; and
identifying the cable in the software routine according to a time interval between the provision of the first voltage and the generation of the trigger signal.

47. The method of claim 46 wherein the step of analyzing the sensor signal comprises the step of analyzing the sensor signal in the microprocessor according to the software routine.

48. The method of claim 44 further comprising:
enabling an operating feature or mode of the electronic instrument as a function of analyzing the identification of the cable.

49. The method of claim 49 wherein the electronic instrument comprises a pulse oximetry monitor.

50. The method of claim 49 wherein the enabling of an operating feature or mode of the electronic instrument comprises enabling a noise or artifact rejecting algorithm in the electronic instrument.

51. A system for providing information based on a sensor signal from a sensor, comprising:
a cable including an elongated signal conduit adapted for coupling to a sensor at one end and to a signal terminal at the other end, the elongated signal conduit adapted for coupling a sensor signal from the sensor terminal to the signal terminal;
a connector attached to the cable adjacent to the signal terminal, the connector having a plurality of terminals;
an inductor coupled to at least one resistor to form a network having predetermined reactance characteristics that is coupled between selected terminals of the connector; and
an electronic instrument coupled to the terminals in the connector, the instrument being adapted to provide the information as a function of the sensor signal and to identify the cable based on a measurement of selected reactance characteristics, the instrument further comprising a microprocessor coupled to one or more of the terminals in the connector to receive the sensor signal, a display coupled to the microprocessor, and a measurement circuit coupled to exchange signals with the microprocessor, wherein the measurement circuit is comprised of a bridge circuit coupled to receive an alternating current signal from the microprocessor, the bridge circuit having a detector outputting a detection signal to the microprocessor and being coupled to receive the selected ones of the terminals in the connector so that the bridge circuit is adapted to detect the reactance characteristics of the network and generate the detection signal in response to the reactance characteristics.

52. A method for identifying a cable having a reactance element with selected reactance characteristics, the method comprising the steps of. providing a first voltage to the reactance element, wherein the reactance element includes an inductor;

monitoring a second voltage in the reactance element to detect a rate of change of the second voltage; and comparing the rate of change of the second voltage to a predetermined rate and identifying the cable based on the comparison.

53. The method of claim 52 wherein the step of monitoring a second voltage in the reactance element comprises the steps of:

coupling the second voltage to a switch to control a state of the switch;

detecting when the state of the switch changes; and determining a time interval between the step of providing a first voltage and the detection of the changed state of the switch.

54. The method of claim 52 wherein the step of detecting when the state of the switch changes comprises the steps of:

applying a voltage to a circuit coupled to the switch; and detecting a change in current in the circuit when the state of the switch changes.

55. A method for identifying a cable having a reactance element with selected reactance characteristics, the method comprising the steps of:

providing a first voltage to the reactance element, wherein the reactance element includes an inductor coupled to a resistor;

monitoring a second voltage in the reactance element to detect a rate of change of the second voltage; and comparing the rate of change of the second voltage to a predetermined rate and identifying the cable based on the comparison.

56. The method of claim 55 wherein the step of monitoring a second voltage in the reactance element comprises the steps of:

coupling the second voltage to a switch to control a state of the switch;

detecting when the state of the switch changes; and determining a time interval between the step of providing a first voltage and the detection of the changed state of the switch.

57. The method of claim 56, wherein the step of detecting when the state of switch changes comprises the steps of:

applying a voltage to a circuit coupled to the switch; and detecting a change in current in the circuit when the stage of the switch changes.

* * * * *

UNITED STATES PATENT AND TRADEMARK OFFICE
CERTIFICATE OF CORRECTION

PATENT NO. : 6,497,659 B1
DATED : December 24, 2002
INVENTOR(S) : Stephen C. Rafert It is certified that error appears in the above-identified patent and that said Letters Patent is hereby corrected as shown below:

Column 2,
Line 1, "medical monitors connect" should read -- medical monitors connecting --
Line 16, "reference. In" should read -- reference. It --

Column 5,
Line 12, "is identified the microprocessor" should read -- is identified, the microprocessor--

Column 6,
Line 48, "A microprocessor is" should read -- A microprocessor 110 is --

Column 10,
Line 7, "Also, a timerelated" should read -- Also, a time-related --
Line 21, "following elements. A" should read -- following elements: A --

Column 11,
Line 43, "as well a other cable" should read -- as well as other cable --
Line 53, "identity the cable" should read -- identify the cable --

Column 12,
Line 25, "invention For example," should read -- invention. For example, --

Column 13,
Line 24, "network and operable" should read -- network having a single polarity and operable --
Line 43, "from the sensor terminal to" should read -- from the sensor to --

Column 15,
Line 6, "The system of claim 29" should read -- The system of claim 27 --
Line 8, "The system of claim 28" should read -- The system of claim 16 --
Line 13, "The system of claim 16" should read -- The system of claim 31 --
Line 21, "comprising the steps of" should read -- comprising the steps of: --
Lines 29, 32, 35, 38 and 41, "The method of claim 29" should read -- The method of claim 35 --
Line 31, "a first voltage to a capacitor." should read -- the first voltage to a capacitor." --
Lines 34 and 40, "a first voltage to a resistor" should read -- the first voltage to a resistor --
Line 37, "providing a first voltage" should read -- providing the first voltage --

UNITED STATES PATENT AND TRADEMARK OFFICE
CERTIFICATE OF CORRECTION

PATENT NO. : 6,497,659 B1
DATED : December 24, 2002
INVENTOR(S) : Stephen C. Rafert It is certified that error appears in the above-identified patent and that said Letters Patent is hereby corrected as shown below:

Column 16,
Line 5, "reactance element the first" should read -- reactance element, the first --
Line 20, "step of monitoring a" should read -- step of monitoring the --
Line 30, "The method of claim 46" should read -- The method of claim 44 --
Line 34, "The method of claim 44" should read -- The method of claim 43 --
Lines 38 and 40, "The method of claim 49" should read -- The method of claim 48 --
Line 50, "from the sensor terminal to" should read -- from the sensor to --

Column 17,
Line 12, "the steps of. providing" should read -- the steps of providing --
Line 30, "The method of claim 52" should read -- The method of claim 53 --

Column 18,
Line 23, "a first voltage" should read -- the first voltage --

Signed and Sealed this

Fourteenth Day of December, 2004

JON W. DUDAS
*Director of the United States Patent and Trademark Office*